US006852532B2

(12) United States Patent
Mayer-Proschel et al.

(10) Patent No.: US 6,852,532 B2
(45) Date of Patent: Feb. 8, 2005

(54) METHOD OF ISOLATING HUMAN NEUROEPITHELIAL PRECURSOR CELLS FROM HUMAN FETAL TISSUE

(75) Inventors: Margot Mayer-Proschel, Pittsford, NY (US); Mahendra S. Rao, Salt Lake City, UT (US); Patrick A. Tresco, Sandy, UT (US); Darin J. Messina, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 447 days.

(21) Appl. No.: 09/813,429

(22) Filed: Mar. 21, 2001

(65) Prior Publication Data

US 2002/0168767 A1 Nov. 14, 2002

(51) Int. Cl.[7] .............................. C12N 5/00; C12N 5/08
(52) U.S. Cl. ...................... 435/368; 435/332; 435/378; 435/325
(58) Field of Search ................................ 435/368, 325, 435/332, 378

(56) References Cited

PUBLICATIONS

Ahmed et al., "BDNF Enhances the Differentiation but Not the Survival of CNS Stem Cell–Derived Precursors", *J. Neurosci.* 1995 15:5765–5778.
Brannen C.L. and Sugaya K., "In vitro differentiation of multipotent human neural progenitors in serum–free medium", *NeuroReport* 2000 11:1123–1128.
Carpenter et al., "In Vitro Expansion of a Multipotent Population of Human Neural Progenitor Cells", *Exp. Neurol.* 1999 158:265–278.
Chiasson et al., "Adult Mammalian Forebrain Ependymal and Subependymal Cells Demonstrate Proliferative Potential, but only Subependymal Cells Have Neural Stem Cell Characteristics", *J. Neurosci.* 1999 19:4462–4471.
Corbeil et al., "The Human AC133 Hematopoietic Stem Cell Antigen Is also Expressed in Epithelial Cells and Targeted to Plasma Membrane Protrusions" *J. Biol. Chem.* 2000 275:5512–5520.
Doetsch et al., "Subventricular Zone Astrocytes Are Neural Stem Cells in the Adult Mammalian Brain", *Cell* 199 97:703–716.
Doetsch et al., "Cellular Composition and Three–Dimensional Organization of the Subventricular Germinal Zone in the Adult Mammalian Brain", *J. Neurosci.* 1997 17:5046–5061.
Eriksson et al., "Neurogenesis in the adult human hippocampus", *Nat. Med.* 1998 4:1313–1317.
Fricker et al., "Site–Specific Migration and Neuronal Differentiation of Human Neural Progenitor Cells after Transplantation in the Adult Rat Brain", *J. Neurosci.* 1999 19:5990–6005.

Forsberg–Nilsson et al., "Platelet–Derived Growth Factor Induces Chemotaxis of Neuroepithelia, Stem Cells", *J. Neurosci. Res.* 1998 53:521–530.
Gage F.H., "Mammalian Neural Stem Cells", *Science* 2000 287:1433–1438.
Gage et al., "Multipotent Progenitor Cells in the Adult Dentate Gyrus", *J. Neurobiol.* 1998 36:249–266.
Garcia–Verdugo et al., "Architecture and Cell Types of the Adult Subventricular Zone: In Search of the Stem Cells", *J. Neurobiol.* 1998 36:234–248.
Haydar et al., "Differential Modulation of Proliferation in the Neocortical Ventricular and Subventricular Zones", *J. Neurosci.* 2000 20:5764–5774.
Horner et al., "Proliferation and Differentiation of Progenitor Cells Throughout the Intact Adult Rat Spinal Cord", *J. Neurosci.* 2000 20:2218–2228.
Johansson et al., "Neural Stem Cells in the Adult Human Brain", *Exp. Cell Res.* 1999 253: 733–736.
Johansson et al., "Identification of a Neural Cell Stem in the Adult Mammalian Central Nervous System", *Cell* 1999 96:25–34,
Kalyani et al., "Neuroepithelial Stem Cells from the Embryonic Spinal Cord: Isolation, Characterization, and Clonal Analysis", *Dev. Biol.* 1997 186:202–223.
Kalyani et al., "Expression of EGF Receptor and FGF Receptor Isoforms During Neuroepithelial Stem Cell Differentiation", *J. Neurobiol.* 1999 38:207–224.
Kirschenbaum et al., "In vitro Neuronal Production and Differentiation by Precursor Cells Derived from the Adult Human Forebrain", *Cereb. Cortex* 1994 4:576–589.
Kukekov et al., "Multipotent Stem/Progenitor Cells with Similar Properties Arise from two Neurogenic Regions of Adult Human Brain[1]", *Exp. Neurol.* 1999 156:333–344.
Lois C. and Alvarez–Buylla A., "Proliferating subventricular zone cells in the adult mammalian forebrain can differentiate into neurons and glia", *Proc. Natl Acad. Sci. USA* 1993 90:2074–2077.
Marmur et al., "Isolation and Developmental Characterization of Cerebral Cortical Multipotent Progenitors", *Dev. Biol.* 1998 204:577–591.
Miraglia et al., "A Novel Five–Transmembrane Hematopoietic Stem Cell Antigen: Isolation, Characterization, and Molecular Cloning", *Blood* 1997 90:5013–5021.

(List continued on next page.)

*Primary Examiner*—Brenda Brumback
*Assistant Examiner*—Robert C. Hayes
(74) *Attorney, Agent, or Firm*—Licata & Tyrrell P.C.

(57) ABSTRACT

A method for isolating human neuroepithelial precursor cells from human fetal tissue by culturing the human fetal cells in fibroblast growth factor and chick embryo extract and immunodepleting from the cultured human fetal cells any cells expressing A2B5, NG2 and eNCAM is provided. In addition, methods for transplanting these cells into an animal are provided. Animals models transplanted with these human neuroepithelial precursor cells and methods for monitoring survival, proliferation, differentiation and migration of the cells in the animal model via detection of human specific markers are also provided.

1 Claim, No Drawings

OTHER PUBLICATIONS

Morrison et al., "Prospective Indentification, Isolation by Flow Cytometry, and In Vivo Self–Renewal of Multipotent Mammalian Neural Crest Stem Cells", *Cell* 1999 96:737–749.

Palmer et al., "Fibroblast Growth Factor–2 Activates a Latent Neurogenic Program in Neural Stem Cells from Diverse Regions of the Adult CNS", *J. Neurosci.* 1999 19:8487–8497.

Pagano et al., "Isolation and Characterization of Neural Stem Cells from the Adult Human Olfactory Bulb", *Stem Cells* 2000 18:295–300.

Piper et al., Immunocytochemical and Physiological Characterization of a Population of Cultured Human Neural Precursors, *J. Neurophysiol.* 2000 84:534–548.

Quinn et al., "Lineage Restriction of Neuroepithelial Precursor Cells from Fetal Human Spinal Cord", *J. Neurosci. Res.* 1999 57:590–602.

Rao M.S., "Multipotent and Restricted Precursors in the Central Nervous System", *Anat. Rec.* 1999 257:137–148.

Reynolds B.A. and Weiss, S., "Clonal and Population Anaylses Demonstrate That an EGF–Responsive Mammalian Embryonic CNS Precursor Is a Stem Cell", *Dev. Biol.* 1996 175:1–13.

Stemple D.L. and Anderson D.J., "Isolation of a Stem Cell for Neurons and Glia from the Mammalian Neural Crest", *Cell* 1992 71:973–985.

Svendsen et al., "A new method for the rapid and long term growth of human neural precursor cells", *J. Neurosci. Methods* 1998 85:141–152.

Tsai R.Y. and Mckay R.D., "Cell Contact Regulates Fate Choice by Cortical Stem Cells", *J. Neurosci.* 2000 20:3725–3735.

Vescovi et al., "Isolation and Cloning of Multipotential Stem Cells from the Embryonic Human CNS and Establishment of Transplantable Human Neural Stem Cell Lines by Epigenetic Stimulation", *Exp. Neurol.* 1999 156:71–83.

Villa et al., "Establishment and Properties of a Growth Factor–Dependent, Perpetual Neural Stem Cell Line from the Human CNS", *Exp. Neurol.* 2000 161:67–84.

Weigmann et al., "Prominin, a novel microvilli–specific polytopic membrane protein of the apical surface of epithelial cells, is targeted to plasmalemmal protrusions of non-epithelial cells", *Proc. Natl Acad. Sci. USA* 1997 94:12425–12430.

Weiss et al., "Multipotent CNS Stem Cells Are Present in the Adult Mammalian Spinal Cord and Ventricular Neuroaxis", *J. Neurosci.* 1996 16:7599–7609.

Yin et al., "AC133, a Novel Marker for Human Hematopoietic Stem and Progenitor Cells", *Blood* 1997 90:5002–5012.

METHOD OF ISOLATING HUMAN NEUROEPITHELIAL PRECURSOR CELLS FROM HUMAN FETAL TISSUE

BACKGROUND OF THE INVENTION

The demonstration that stem cells exist in the adult brain and spinal cord (Chiasson et al. J. Neurosci. 1999 19:4462–71; Doetsch et al. Cell 1999 97:703–16; Gage et al. J. Neurobiol. 1998 36:249–66; Johansson et al. Exp. Cell Res. 1999 253: 733–6; Kukekov et al. Exp. Neurol. 1999 156:333–44; Pagano et al. Stem Cells 2000 18:295–300; Palmer et al. J. Neurosci. 1999 19:8487–97; Weiss et al. J. Neurosci. 1996 16:7599–609), that neurogenesis and gliogenesis are ongoing processes (Eriksson et al. Nat. Med. 1998 4:1313–7; Horner et al. J. Neurosci. 2000 20:2218–28; Johansson et al. Cell 1999 96:25–34; Kirschenbaum et al. Cereb. Cortex 1994 4:576–89) and that stem cell populations can be modulated by extrinsic signals (Ahmed et al. J. Neurosci. 1995 15:5765–78; Forsberg-Nilsson et al. J. Neurosci. Res. 1998 53:521–30; Johe et al. Genes Dev. 1996 10:3219–40; Kalyani et al. Dev. Biol. 1997 186:202–23; Palmer et al. J. Neurosci. 1999 19:8487–97; Tsai, R. Y. and McKay, R. D. J. Neurosci 2000 20:3725–35; Vescovi et al. Exp. Neurol. 1999 156:71–83; Weiss et al. J. Neurosci. 1996 16:7599–609), has lead to a plethora of publications characterizing multipotent neural stem cells (NSCs)(Johansson et al. Exp. Cell Res. 1999 253:733–6; Kalyani et al. December Biol. 1997 186:202–23; Morrison et al. Cell 1999 96:737–49; Reynolds, B. A. and Weiss, S. Dev. Biol. 1996 175:1–13; Stemple, D. L. and Anderson, D. J. Cell 1992 71:973–85;Vescovi et al. Exp. Neurol. 1999 156:71–83; Weiss et al. J. Neurosci. 1996 16:7599–609). What has become clear is that several classes of multipotent cells exist, all of which are nestin immunoreactive and capable of differentiating into astrocytes, neurons and oligodendrocytes. Different populations of cells can be distinguished by differences in culture conditions, self-renewal capability, as well as in their ability to integrate and to differentiate following transplantation (Gage, F. H. Science 2000 287:1433–8; Rao, M. S. Anat. Rec. 1999 257:137–48).

Rodents NSCs isolated from different regions of the rostrocaudal axis and at different developmental stages exhibit differences in differentiation potential, growth factor dependence and gene expression. For example, stem cells isolated at an early stage of embryogenesis from the developing spinal cord appear to require fibroblast growth factor (FGF) for survival, while stem cells isolated from more rostral portions at later developmental stages seem equally responsive to FGF and/or to epidermal growth factor (EGF) (Reynolds, B. A. and Weiss, S. Dev. Biol. 1996 175:1–13). Cells isolated from the ventricular zone express GFAP as a marker in the adult (Doetsch et al. Cell 1999 97:703–16) while multipotent cortical stem cells express polysialated NCAM (Marmur et al. Dev. Biol. 1998 204:577–91). Responses to neurotransmitters also appear different. Ventricular zone stem cells proliferate in response to glutamate while subventricular zone stem cell turnover is reduced (Haydar et al. J. Neurosci 2000 20:5764–74). FGF-dependant stem cells can generate EGF-dependent cells in vitro, suggesting that these cells may represent different developmental stages. The lineage relationship between these various cells remains to be determined.

Less is known about human neural stem cells (hNSCs) isolated from fetal and adult tissue (Brannen, C. L. and Sugaya, K. Neuroreport 2000 11:1123–8; Carpenter et al. Exp. Neurol. 1999 158:265–78; Flax et al. Nat. Biotechnol. 1998 16:1033–9; Johansson et al. Exp. Cell Res. 1999 253:733–6; Kukekov et al. Exp. Neurol. 1999 156:333–44; Pagano et al. Stem Cells 2000 18:295–300; Vescovi et al. J. Neurotrauma 1999 16:689–93; Vescovi et al. Exp. Neurol. 1999 156:71–83; Villa et al. Exp. Neurol. 2000 161:67–84). These cells give rise to glia and neurons, can be grown under different culture conditions and show different growth factor requirements. The lineage relationship among the various identified hNSCs and their relationship to previously described rodent stem cell populations remains to be determined. Indeed, comparative studies of rodent and human-derived stem cells have been hampered by the limited availability of cross-reactive reagents. For example, the monoclonal antibody nestin does not react with human cells and AC133, a recently identified stem cell marker, does not cross react with rat-derived NSC's (Uchida et al. *Keystone Symposium* 2000).

Recently, hNSCs have become available through commercial sources such as Clonetics (San Diego, Calif.) and Clonexpress (Gaithersberg, Md.). First passage cells and growth conditions are available that generate neurons, astrocytes and possibly oligodendrocytes. Cells from Clonexpress have a limited differentiation capacity and generate cells that co-express neuroglial markers (Piper et al. J. Neurophysiol. 2000 84:534–48).

Methods have now been developed for isolating and propagating a tripotential human precursor cell which, upon characterization, has been shown to share many features with a rodent-derived neuroepithelial precursor (NEP) (Kalyani et al. Dev. Biol. 1997 186:202–231 Kalyani et al. J. Neurobiol. 1999 38:207–24). Like rodent-derived NEPs, hNEPs can be grown as adherent cultures in FGF/chick embryo extract (CEE) and do not require leukemia inhibitory factor (LIF) or EGF for proliferation and survival. These cells can be induced to differentiate into astrocytes, neurons and oligodendrocytes in culture. A subset of the hNEPs express AC133 and a small percentage are also GFAP positive. Further, hNEPs transplanted into the intact adult rat brain survive, can be identified with human-specific antibodies, proliferate, differentiate into neurons and glia and migrate extensively in a context dependent manner.

SUMMARY OF THE INVENTION

An object of the present invention is to provide a method for isolating and propagating human neuroepithelial precursor cells from a heterogeneous population of human fetal cells. In the method of the present invention, commercially available human fetal cells are cultured with fibroblast growth factor (FGF) and chick embryo extract (CEE). Cells expressing A2B5, NG2 and eNCAM are then immunodepleted to enrich for a population of human neural precursor or stem cells.

Another object of the present invention is to provide a method for transplanting into the central nervous system of an animal human neuroepithelial precursor cells isolated via culturing of human fetal cells in FGF and CEE followed by immunodepletion of any cells expressing A2B5, NG2 and eNCAM from the culture.

Another object of the present invention is to provide nonhuman animal models for studying transplantation of human neural stem cells in the central nervous system. Nonhuman animal models of the present invention are produced by transplanting into their central nervous systems human neuroepithelial precursor cells isolated via culturing of human fetal cells in FGF and CEE followed by immunodepletion of any cells expressing A2B5, NG2 and eNCAM from the culture.

Yet another object of the present invention is to provide human specific markers and methods for monitoring survival, proliferation, differentiation and migration of human neuroepithelial precursor cells in an animal model transplanted with human neuroepithelial precursor cells via detection of these human specification markers. For purposes of the present invention, human specific markers include human NCAM, GFAP, human nuclear antigen and human mitochondria.

DETAILED DESCRIPTION OF THE INVENTION

Human fetal tissue is commercially available from fetuses age 14 to 20 weeks of age, a stage at which neurogenesis predominantly occurs. At this stage, neuron-restricted precursors are present and the number of stem cells is significantly diminished. Thus, unlike neural tissue obtained from rodents prior to closure of the neural tube, only a small subset of cells in commercially available human fetal tissue age 14–20 weeks are lineage negative cells with characteristics of human neuroepithelial precursor cells. Accordingly, methods used to isolate neuroepithelial precursor cells in nonhuman animals are not directly applicable to isolating human neuroepithelial precursor cells from commercially available sources of human fetal tissue.

The present invention relates to a new method for isolating human neuroepithelial precursor cells (hNEPs) from human fetal tissue age 14 to 20 weeks. In this method, the small subset of precursor cells is selected via immunodepletion of differentiated cells and culture conditions modified from those taught for rodent NEPs to be species specific. Specifically, the human fetal cells are first grown in adherent culture in the presence of fibroblast growth factor (FGF) and chick embryo extract (CEE). Cells expressing A2B5, NG2 and eNCAM are then depleted to enrich the population of multipotent precursor cells, approximately 50% of which stain for AC133/2.

Experiments were first performed to examine the heterogeneous population of neural cells present in human fetal cells 14 to 20 weeks of age. In these experiments, lineage specific markers were used to analyze human fetal cells from various stages of gestation. Cells were cultured directly onto fibronectin/laminin coated multiwell plates in manufacturer's media and fixed 24 hours after seeding. Results shown in Table 1 are from cells obtained at 19 weeks of gestation and are representative of all ages tested.

TABLE 1

In vitro charcterization of Human Fetal Cells

| Antibody | Human Fetal Cells |
|---|---|
| BIII tubulin | 14.0% ± 1.4% |
| GFAP | 42.0% ± 3.8% |
| AC-133/2 | 0% |
| eNCAM | 17.4% ± 2.1% |
| NG2 | 0% |
| A2B5 | 48.1% ± 2.9% |

As shown in Table 1, cultured fetal cells are a mixed population containing a small percentage of BIII-tubulin positive neurons (14%). A nearly identical percentage of cells expressed eNCAM (17.4%) and double-labeling experiments indicated that these markers were primarily co-expressed. A larger percentage of cells were GFAP immunoreactive (42%) and an equivalent percentage expressed A2B5 immunoreactivity. No immunoreactivity for NG-2, AC133/2, Ran-2, GD-3, O4 or Gal-C was detected. A small proportion of cells did not label with A2B5, GFAP or BIII-tubulin. These cells represented candidate precursor cells.

Several different culture conditions were then examined for their ability to enrich for the unlabeled precursor population. Significant enrichment was obtained when cells were grown in the presence of FGF and CEE. More specifically, cells were grown as adherent cultures on fibronectin/laminin coated dishes in DMEM/F12 medium containing additives under similar conditions as described for rat cells by Bottenstein and Sato (Proc. Natl Acad. Sci. USA 1979 76:514–7). It was found that the human cells required a relatively high concentration of FGF for their survival. Preferred concentration of FGF demonstrated to promote survival range from about 10 to about 50 ng/ml. The addition of CEE, preferably from about 5 to about 20% reduces the number of differentiated cells present. Under these culture conditions a significant percentage of cells began to express AC133/2 immunoreactivity (53.2%). In addition, expression of NG-2 was detected. Table 2 provides a comparison of the fetal cell populations before and after culturing in the presence of FGF and CEE.

TABLE 2

Comparison of In Vitro Characteristics of Human Fetal Cells

| Antibody | Human Fetal Cells | Human Fetal Cells cultured in FGF + CEE |
|---|---|---|
| BIII tubulin | 14.0% ± 1.4% | 20.7% ± 2.3% |
| GFAP | 42.0% ± 3.8% | 59.2% ± 4.2% |
| AC-133/2 | 0% | 53.2% ± 6.0% |
| eNCAM | 17.4% ± 2.1 | 21.8% ± 2.2% |
| NG2 | 0% | 45.8% ± 4.4% |
| A2B5 | 48.1% ± 2.9% | 51.6% ± 3.7% |

Following culturing in FGF and CEE, the undifferentiated population was purified by immunopanning and flow-activated cell sorting to remove eNCAM+, NG2+ and A2B5+ cells. Sorted and panned cells did not express eNCAM, A2B5 or NG-2. A subset of the cells continued to express AC133/2 and GFAP. It is believed that AC133/2 is expressed by a subset of precursor cells. This is consistent with recent reports that show that AC133 can be used to isolate precursor cells (Corbeil et al. J. Biol. Chem. 2000 275:5512–20; Miraglia et al. Blood 1997 90:5013–21; Weigmann et al. Proc. Natl Acad. Sci. USA 1997 94:12425–30; Yin et al. Blood 1997 90:5002–12). It was found that of the 50% of human neural precursor cells exhibiting AC133/2 immunoreactivity, many differentiated into oligodendrocytes in culture. This is indicative of the possibility that AC133 may recognize a more restricted precursor population, while a less restricted and more primitive precursor population may be AC133 negative.

The cells are referred to herein as human neuroepithelial precursor cells or hNEPs based on their overall similarity to rodent neuroepithelial precursor cell cultures described by Kalyani et al. (Dev. Biol. 1997 186:202–23). The hNEPs of the present invention comprise a homogenous population of human precursor cells wherein 100% of the cells are immunoreactive with nestin, but are not immunoreactive with NG-2, eNCAM or A2B5. Like rodent NEPS, hNEPs isolated via the method of the present invention appear fibroblastic, divide rapidly in culture, and can be maintained in an undifferentiated state over multiple passages. hNEPs can be induced to differentiate into neurons, astrocytes and oligodendrocytes using different culture conditions. For example, treatment with bFGF and NT3 resulted in a high percentage of BIII-tubulin positive cells indicating the potential for neuronal differentiation. Cells cultured for 5 days in the presence of fetal calf serum stained positively for GFAP and presented a morphology consistent with the presence of astrocytes in culture. The GFAP-positive (GFAP+) cells exhibited a variety of morphologies including bipolar and stellate cells. In addition, cells that were more well-spread displayed discrete GFAP+ filament bundles typical of mature astrocytes in culture. Cells treated with bFGF for 2 days and then switched to a medium containing PDGF and T3 for 7 days stained positively with antibodies against O4 consistent with the presence of oligodendrocytes in culture.

Comparison of hNEPs isolated through the method of the present invention with other multipotent stem cells revealed a number of clear-cut differences. For example, unlike other previously described human stem cell populations, these cells do not require EGF for their survival and proliferation (Carpenter et al. Exp. Neurol. 1999 158:265–78; Fricker et al. J. Neurosci. 1999 19:5990–6005; Quinn et al. J. Neurosci. Res. 1999 57:590–602; Reynolds, B. A. and Weiss, S. Dev. Biol. 1996 175:1–13; Villa et al. Exp. Neurol. 2000 161:67–84). Further, unlike the cells described by Carpenter et al. (Exp. Neurol. 1999 158:265–78), these cells do not require LIF for their proliferation. hNEPs also readily grow as adherent cultures and can be passaged using EDTA alone. Only a small amount of cell death is observed when cells are passaged in this way compared to the large amount of cell death observed when neurosphere type cultures are treated similarly (Svendson et al. J. Neurosci. Methods 1998 85:141–52).

The hNEPs isolated via the method of the present invention have been demonstrated to act as multipotent precursor cells capable of differentiating into neurons, astrocytes and, to a limited extent, oligodendrocytes, not only in vitro but also following transplantation into the intact adult rat subventricular zone and striatum.

In in vitro experiments, growth factor withdrawal promoted differentiation of hNEPs. Neuronal markers appeared early followed by astrocytic and oligodendrocytic markers. Neurons constituted approximately 20% of the cells. The remaining cells appeared undifferentiated even under differentiation conditions, i.e. removal of FGF and CEE and addition of retinoic acid. Despite exposing the cells to several well established tests for inducing differentiation, no bias of differentiation towards any particular lineage other than astrocytes could be achieved. Serum exposure converted virtually the entire population to GFAP positive cells. Promotion of myelination in culture was also not achieved. Oligodendrocytes as identified by O4 or Gal-C did not appear to survive for prolonged periods and myelin markers such as MBP and PLP were undetectable even after co-culture with rat neurons. Thus, it is believed that human oligodendrocyte precursors require specific signals for maturation that were absent in the culture conditions used.

The ability to differentiate hNEPs and rat NEP cells in culture permitted testing of markers that are expressed at different stages of development and comparison of their expression on rat versus human cells. Several markers of immense value in transplant experiments were identified via this comparison. For example, it was found that human specific NCAM, GFAP, human nuclear antigen and human mitochondria can be used to follow transplanted human cell populations. Furthermore, human neural cell adhesion molecule (hNCAM) and human glial fibrillary acidic protein (hGFAP) are extremely useful in providing a dual label that not only identified the cell as human but also identified its phenotype. Table 3 provides a summary of markers useful in identifying, monitoring and determining the phenotype of human cells following transplantation of hNEPs in animal models. Each antibody was tested on cultures of rat CNS cells to assess cross-reactivity issues. Results are summarized in Table 3.

TABLE 3

Immunohistochemical Characterization of Human Neuroepithelial Precursors

| Antibody | Specificity | In Vitro | In Vivo | Rat Cross Reactivity In Vitro |
|---|---|---|---|---|
| BrdU | Dividing Cells | +/− | +/− | + |
| AC-133/2 | Hu stem cells/progenitors | +/− | +/− | − |
| hMito | Hu mitochondria | + | + | − |
| MAB 1281 | Hu nuclei | + | + | − |
| HNCAM | Hu neural cell adhesion molecule | − | +/− | − |
| BIII tubulin | Rat and Hu neurons | − | +/− | + |
| HGFAP | Hu glial fibrillary acidic protein | +/− | +/− | − |
| GFAP | Rat and Hu GFAP | +/− | +/− | + |
| MAB 328 | Rat and Hu oligos/myelin | − | +/− | + |

Note:
+/− gaining refers to staining that does not label all human cells.

Accordingly, also provided in the present invention are methods for monitoring survival, proliferation, differentiation and migration of human cells following transplantation of hNEPs into animal models. For example, survival of hNEPs transplanted into the adult rat brain and their identification can be performed via species-specific antibodies such as antibodies specific for human specific NCAM, GFAP, human nuclear antigen or human mitochondria. The localization of transplanted hNEPs is first ascertained at various days post-transplantation via BrdU staining which identifies pre-labeled hNEPs. For example, at 2 and 7 days post-transplantation, in vitro staining of samples of transplanted cells showed approximately 70% BrdU labeling efficiency. Human-specific markers, as described in Table 3, are then utilized to locate and identify transplanted hNEPs. The MAB 1281, a marker specific for human nuclei (hNuc), and hMito, a marker for human mitochondria, can be used to identify transplanted hNEPs along the injection tract and in adjacent host tissue. Several other markers can be used to identify subpopulations of the transplanted hNEPs and to reflect the capacity of these cells to retain a progenitor status, as well as to differentiate into neurons and glia. Anti-AC133/2, shown, supra, to label a subpopulation of the transplanted hNEPs, can be used to determine whether any hNEPs retain AC133/2 immunoreactivity in situ. At 2 and 7 days post-transplantation, the pattern of staining for AC133/2 positive cells coincides with DAPI nuclear labeling. Human NCAM staining is useful in identifying a subset of those transplanted hNEPs that have differentiated along the neuronal-restricted lineage. Human-specific GFAP antibody can be used to identify human astrocytes in situ. In addition, distinctive perikaryal staining can be used to identify cell bodies and process labeling can be used to identify long processes with multiple varicosities.

Further provided in this invention are methods for using hNEP cells isolated in accordance with the method of the present invention for transplantation into the central nervous system of animals, including, but not limited to, experimental animal models as well as humans. Until now, human to animal model transplantation studies have been hampered by the limited availability of cross-reactive reagents. However, the ability of isolate hNEPs via the method of the present invention has enabled identification of several markers specific to human cells including antibodies to human nuclei, human mitochondria, human-specific NCAM and human-specific GFAP.

Using both lineage-specific and human-specific markers, transplanted hNEPs isolated in accordance with the method of the present invention were demonstrated to survive transplantation in the intact adult rat brain and to have the capacity to generate neurons, astrocytes and a limited number of oligodendrocytes. In the case of hNEP-derived astrocytes, differentiation appeared to be regionally specific. The continued presence of undifferentiated transplanted human hNEPs, identified by the lack of more mature lineage-restricted markers, suggests that early precursors are still present at 28 days following transplantation and are associated with proliferative areas of the intact adult rat brain. In all, undifferentiated and more differentiated hNEP cell derivatives appeared to integrate in a non-disruptive manner into many types of adult brain tissue.

hNEPs, or their progeny, were also found to continue to divide after transplantation. However, no evidence of uncontrolled proliferation including masses, heterotopias or tumors were observed. In fact, even the initial injection tract contained only a small number of cells one month after transplantation indicating that cells either migrated away or responded to endogenous signals.

hNEPs were also found to migrate quite extensively, but not randomly. Cells preferentially followed three paths when transplanted into the SVZa: an anterior stream towards the olfactory bulb; a directed stream of cells to the ventricular zone; and a posterior stream along the corpus callosum towards the occipital cortex. Little migration into the hippocampus, cerebellum or cortex was seen. Transplants into the striatum showed much more limited migration, which was primarily astrocytic and involved migration through the parenchyma. Overall these results indicate that hNEPs and their derivatives follow endogenous cues or permissive paths. The ability to travel down the RMS suggests that hNEPs or their derivatives can follow non-radial glial pathways of migration.

In addition, mature neurons were observed after only a month following transplantation. These cells clearly matured during this time period, extended processes and appeared to integrate, indicating that transplanting cells into immunosuppressed intact rat brain may be a useful model for studying the developmental biology of human precursor cells, as well as for evaluation of the many potential therapeutic uses of these cells.

Finally, while differentiation of hNEPS into oligodendrocytes was minimal, oligodendrocytes were observed along the injection tract, presumably because of local damage caused by the injection. Thus, it is believed that hNEPs will like readily myelinate in an appropriate model and have begun experiments to test this possibility.

All of the transplantation studies were performed with freshly panned and sorted hNEPs. BrdU pre-labeling, at approximately 70% labeling efficiency, was used to identify transplanted cells at 2 and 7 days. Other animals grafted with unlabeled cells were examined at 28 days using human specific markers. Transplanted BrdU-positive cells were observed in all animals at 2 and 7 days post-transplantation in all graft sites and in the respective injection tracts. In addition, transplanted cells could be identified using human specific antibodies directed against hNCAM, hGFAP, hMito and hNuc. All transplanted animals (n=36) exhibited evidence of differentiation that varied with the site of transplantation and the time of sacrifice.

Transplanted human NEP cells differentiated into neurons and glia following transplantation into intact adult SVZa and striatum. Grafted cells were examined with both cell type and human specific markers following transplantation (Table 3). Soon after grafting (2 days), large numbers of BrdU-labeled cells were observed at both sites. A small number of BrdU-labeled cells stained for GFAP, however, the majority of cells did not react with any of the markers listed in Table 3 indicating that many of the grafted cells remained undifferentiated 48 hours following implantation. Human specific GFAP-labeled (hGFAP+) cells exhibited a unipolar morphology irrespective of the site of transplantation. The hGFAP-labeled processes appeared much shorter and thicker than any of the endogenous populations of astrocytes as determined by a comparative analysis of the staining pattern obtained with non-species specific polyclonal antisera to GFAP. These results indicate that 48 hours after transplantation, the majority of cells remained undifferentiated, while a small portion had differentiated into astrocytes, but none into mature neurons or oligodendrocytes.

At later time points (7 and 28 days), larger numbers of grafted cells stained for neuron-specific and astrocyte-specific markers, while only a small subset of cells labeled for oligodendrocyte markers. Human specific NCAM-and hNuc/BIII tubulin-double positive cells and their processes were observed at both graft sites, in the adjacent parenchyma and in the white matter, suggesting that many of the cells differentiated into neurons. These cells possessed unipolar, bipolar and multi-polar processes that in some cases extended hundreds of microns into the cortex, along white matter tracts and into the RMS. A comparison of hNCAM and hNuc/BIII tubulin+ cells at 2, 7 and 28 days indicated that both the number of cell bodies as well as the length and complexity of their processes increased over time, suggesting that cell growth/hypertrophy followed differentiation and that this process increased in incidence over time. Human specific GFAP-positive cells were observed at both graft sites, throughout the ipsilateral corpus callosum extending to the occipital cortex and ipsilateral striatum. At least three distinct phenotypes were apparent, which appeared to be regionally specific. HGFAP-labeled cells in the striatum had a stellate morphology similar to those of the endogenous population, many of which appeared to contact blood vessels. HGFAP-positive cells located along the length of the callosum had long processes similar to the endogenous population of white matter astrocytes, while hGFAP labeled cells located at the wall of the lateral ventricle had processes which extended toward the ependyma in a manner similar to the endogenous population, but with processes that were much thicker. While a significant subset of cells labeled for neuron and astrocyte markers, only a few cells expressed markers consistent with an oligodendrocyte phenotype. When MAB 328 antibody coupled with antisera to human nuclear antigens were used to detect human specific oligodendrocyte differentiation, MAB 328/hNuc-double labeled cells were observed only where the injection tract penetrated the corpus callosum. Differentiation into oligodendrocytes is believed to be induced by damage from the penetrating stab wound through the white matter. However, the small number of MAB 328/hNuc-double labeled cells indicated that a very limited amount of oligodendrocyte differentiation had occurred.

Not all of the transplanted cells labeled with lineage-restricted markers. At 2 and 7 days, significant numbers of BrdU-labeled cells, which double labeled with antisera against human mitochondrial antigens (hMito), did not double label with other markers listed in Table 3. Thus, many cells remained undifferentiated. These cells were present at all grafts sites, injection tracts, as well as in the ipsilateral subependymal zone, corpus callosum, and in the ipsilateral RMS. Similarly, at 28 days, a significant number of hNuc-labeled cells did not co-label with other cell type specific markers. However, at day 28, larger numbers of these cells were observed along the wall of the ipsilateral lateral ventricle, in the ipsilateral RMS, and in the corpus callosum extending, in some cases, toward the occipital cortex. The presence of hNEP cells in the subependymal zone of the ipsilateral lateral ventricle and in the RMS at 28 days indicates that a subset of the grafted cells had integrated and continued to proliferate in a manner similar to the endogenous population of precursor cells.

To assess whether hNEP cells continued to proliferate following transplantation, two separate experiments were performed. BrdU-labeled cells were implanted and analyzed following transplantation (N=19). Several pieces of evidence indicate that transplanted HNEP cells continue to proliferate following transplantation into intact adult SVZa and striatum. At both graft sites, the number of BrdU-labeled cells decreased with time from transplantation, while the number and distribution of cells labeled with human-specific antisera increased. In the latter case many hNuc-positive cells remained undifferentiated as determined by a lack of staining with cell type specific or lineage-restricted markers, thus indicating that early precursors continued to be generated over time. At all time points at both grafts sites, intensely labeled BrdU-positive cells were surrounded by less intensely labeled BrdU+ cells that were often distributed at the periphery of the grafted cell mass.

To further assess the potential of hNEPs to divide in situ, BrdU was injected i.p. one day prior to the sacrifice of 28 day old grafts (N=8) and compared with BrdU distribution in non-transplanted, BrdU-injected control animals (N=3). At 28 days, BrdU-positive cells were identified near the injection site and along the injection tracts in areas where no BrdU-labeled cells were observed in non-transplanted control animals indicating that cell proliferation continued at the graft site. Lastly, a large number of hNuc-labeled cells that did not co-label with more mature lineage-restricted markers were observed in the subventricular zone suggesting that these cells had integrated and continued to divide in an effort to function as those previously identified endogenous neural stem cells of the SVZa (Doetsch et al. Cell 1999 97:703–16; Doetsch et al. J. Neurosci. 1997 17:5046–61; Garcia-Verdugo et al. J. Neurobiol. 1998 36:234–48; Goldman et al. J. Neeurooncol. 1995 24:61–4; Lois, C. and Alvarez-Buyll, A. Proc. Natl Acad. Sci. USA 1993 90:2074–7).

Migration of hNEP cells following transplantation in the intact adult rat brain was region-specific. The distribution of BrdU-labeled cells, as well as those identified with human-specific antisera, indicated that grafted human NEP cells migrated extensively along the ipsilateral rostral-caudal axis. In addition, the distribution of cells over time was graft-site dependent. In SVZa grafted animals at 2 days, intensely BrdU-labeled cells were restricted to the anterior subventricular zone below the corpus callosum within the injection tract, the corpus callosum, and extended medially to surround the rostral and lateral aspect of the lateral ventricle. The nuclei of cells in the corpus callosum were elliptical in shape and oriented along the white matter. At 7 days, hNEPs were observed in the ipsilateral rostral migratory stream (RMS) extending into the olfactory bulb. These cells displayed an ovoid-shaped nucleus and were aligned along the rostral-caudal axis of the RMS, suggesting rostral migration with features consistent with the behavior of endogenous cells. At 28 days, large numbers of hNEPs labeled with antisera against BrdU, hNuc and hMito were found throughout the subventricular zone and all levels of the RMS extending into the ipsilateral olfactory bulb. Many of the cells located in the RMS exhibited a bipolar morphology and labeled with antisera against BIII tubulin and human-specific NCAM. In addition, transplanted cells identified with hGFAP immunoreactivity were dispersed along the rostral-caudal axis of the corpus callosum, indicating that cells also had migrated medially and laterally along the white matter, in some cases extending caudally to the occipital cortex. HGFAP-positive cells in white matter exhibited extensive processes similar to endogenous white matter astrocytes.

Cells grafted into the striatum displayed a different pattern of migration. At both 2 and 7 days, the majority of grafted cells were restricted to the graft site as a deposit of cells that stained positively for hNuc/BIII, hNCAM and hGFAP. Additionally, unlike those cells transplanted in the SVZa, the nuclei of these cells did not exhibit an elliptical morphology. By 28 days, however, transplanted hNEPs were found distributed throughout the ipsilateral striatum, along the more caudal aspects of the corpus callosum, the caudal subependymal zone of the lateral ventricle and posteriorly toward the occipital cortex. The transplanted cells appeared to be migrating in a radial pattern about the site of implantation. The majority of cells were hGFAP positive. In addition, hNEPs could also be found migrating posteriorly along the border of the fimbria and the caudal striatum near the wall of the lateral ventricle. Similar to the RMS, many undifferentiated BrdU+ cells were found. These cells were present in a chain-like fashion with elliptical nuclei oriented in the rostral-caudal axis. Human mitochondrial staining further revealed that these cells had mitochondria-rich processes aligned along the plane of the ventral hippocampal commissure, indicating that these transplanted hNEPs were migrating to the hippocampus. A small number of transplanted BrdU+ cells were also found incorporating into the ependymal lining of the posterior region of the lateral ventricle.

Thus, as demonstrated herein, the hNEPs isolated in accordance with the method of the present invention are useful in developing nonhuman animal models for the study of transplantation of these human cells into the central nervous system. For purposes of the present invention, by nonhuman animal it is meant any animal with a central nervous system comprising a brain and spinal cord. In a preferred embodiment, the animal model comprises a rodent, such as a rat or mouse, a lagomorph, a canine or a primate. However, as will be understood by those of skill in the art upon reading this disclosure, other animals identified as useful in the study of central nervous system cell transplantations can also be used. In the animal models of the present invention, hNEPs isolated from human fetal tissue in accordance with the method described herein are transplanted into either the brain or spinal cord of the animal. The transplanted hNEPS can then be monitored for survival, proliferation, differentiation, and migration via the methods and markers described herein.

Expansion and purification of a human-derived multipotent precursor derived from a commercially available source of fetal tissue will also facilitate the development of cell-based therapies for the restoration of CNS tissue function in humans. As demonstrated herein, hNEP cells isolated via the method of the present invention survive, proliferate, migrate and differentiate in vivo in an animal model for transplantation. Based upon these animal experiments, it is expected that the cells will function similarly when transplanted into the central nervous system of humans. Accordingly, the hNEP cells isolated in accordance of the method of the present invention are expected to useful in conditions wherein replacement of neural cells is needed. Examples of such conditions include, but are not limited to, Parkinson's disease, Huntington's disease, stroke and epilepsy. Several clinical trials with other neural cell types are currently being conducted for these diseases. Similar protocols and procedures used in these clinical trials with other neural cells can be adapted routinely by those of skill in the art for use with the hNEPs of the present invention.

The following nonlimiting examples are provided to further illustrate the present invention.

EXAMPLES

Example 1

Culture of Human Neural Stem Cells

Human neural progenitor cells derived from fetal tissue were acquired from Clonetics (San Diego, Calif.). Frozen aliquots of cells were thawed and plated on fibronectin/laminin-coated multiwell dishes in Neural Progenitor Cell Basal Medium (NPBM, Clonetics) supplemented with human recombinant basic fibroblast growth factor, human recombinant epidermal growth factor, neural survival factors, 5 mg/ml gentamicin and 5 $\mu$g/ml amphotericin-B (Singlequots, Clonetics). Cultures were incubated at 37° C., 5% $CO_2$ and fixed 24 hours later. These wells were subsequently processed for immunocytochemistry to assess the starting population of Clonetics cells. In parallel, Clonetics cells were thawed and immediately plated on fibronectin/laminin-coated flasks (Greiner) and cultured in Neuroepithelial Precursor (NEP) medium that consisted of DMEM-F12 (Life Technologies, Grand Island, N.Y.) supplemented with additives as described by Bottenstein and Sate (Proc. Natl Acad. Sci. USA 1979 76:514–7), basic fibroblast growth factor (bFGF, 10 ng/ml, Peprotech, Rocky Hill, N.J.) and chick embryo extract (CEE, 10%) prepared as described by Stemple and Anderson (Cell 1992 71:973–85). Unattached cells typically formed floating spheres. After 24 hours in culture, spheres were removed, gently triturated and re-combined with the attached cells. NEP media was exchanged every other day.

Example 2

Isolation of Human Neuroepithelial Precursor Cells (hNEPs)

After 5 days in culture, immunopanning and flow-activated cell sorting were used to remove eNCAM$^-$, NG2$^+$, and $A_2B_5^-$ cells. Briefly, cells were treated with 5 mM EDTA (Life Technologies) and the suspension plated on an eNCAM antibody (5A5, Developmental Studies Hybridoma Bank)-coated dish to allow binding of all eNCAM$^+$ cells to the plate. ENCAM antibody-coated dishes were prepared by sequentially coating tissue culture dishes with an unlabeled anti-mouse IgM antibody (10 $\mu$g/ml) overnight, rinsing dishes with DPBS, followed by coating with 5A5 hybridoma supernatant for 1–3 hours at 37° C. Plates were washed twice with DPBS prior to plating neural progenitor cells. After a 30 minute exposure period, unbound cells (eNCAM cells) were removed and plated onto a dish coated with antibodies to NG2 for 30 minutes. NG2 panning dishes were made by coating dishes with an NG2 antibody (1:50) for 1–3 hours at 37° C. The supernatant was then removed (eNCAM/NG2 cells) and immunostained for $A_2B_5$. Cells were exposed to antibodies to $A_2B_5$ (1:2, Developmental Studies Hybridoma Bank) in NEP media for 1 hour to stain the membranes of live $A_2B_5^+$ cells. All cells were then sent through a flow-activated cell sorter to remove the population of $A_2B_5^+$ cells. After sorting, the negative population (human NEPs) was propagated in NEP media on fibronectin/laminin coated T-75 flasks prior to transplantation studies. NEP media was exchanged every other day.

Example 3

Generation of Neurons, Oligodendrocytes and Astrocytes from hNEPs

Panned/sorted populations of human NEPs were plated on fibronectin/laminin-coated 12 mm coverslips in various conditions to promote differentiation. Coverslips were fixed with 4% paraformaldehyde at the times established below. To induce neuronal differentiation, cells were exposed to bFGF 10 ng/ml) and NT3 (10 ng/ml, Peprotech). After 5 days in culture, fixed cultures were stained using antibodies to $\beta$-III tubulin to assess the capacity of these cells to differentiate into neurons. For oligodendrocyte differentiation, cells were plated in a bFGF (10 ng/ml)—containing medium for 2 days and then were switched to a medium containing PDGF (10 mg/ml, Upstate Biotech, Waltham, Mass.) and T3 (50 nM, Sigma Chemical Co. St. Louis, Mo.) for 7 days. Antibodies to O4 were used to identify oligodendrocytes in culture. For astrocytic differentiation, cells were cultured for 5 days in the presence of fetal calf serum (10%, Life Technologies). Fixed cultures were stained with antibodies to GFAP to identify mature astrocytes.

Example 4

Immunocytochemistry

Cultures were stained using antibodies against $A_2B_5$ (1:2, Developmental Studies Hybridoma Bank), AC133/2 (1:100, Miltenyi Biotec, Auburn, Calif.), $\beta$-III tubulin (1:1000, Sigma), eNCAM (1:2, 5A5, Developmental Studies Hybridoma Bank), GFAP (1:2000, Dako, Carpinteria, Calif.), NG2 (1:50), and O4 (1:2, BMB hybridoma). Following fixation, cultures were treated with 0.5% Triton (Triton X-100, Sigma) in PBS for 2 minutes to access intracellular antigens. Fixed coverslips or plates were then treated with primary antibodies in a blocking solution containing Hank's balanced salt solution and 5% calf serum for 1 hour at room temperature. Following 3 washes with PBS, cultures were incubated in the appropriate secondaries (1:220) conjugated to either Texas Red or Alexa 488 (Molecular Probes, Eugene, Oreg.) for 1 hour at room temperature. AC133/2 staining required amplification with a biotinylated secondary, followed by a streptavidin-alexa 488 conjugated tertiary. All cultures were counterstained with DAPI (Molecular Probes) to identify cell nuclei.

Example 5

Cell Preparation for Transplantation

One day prior to transplantation, cultured human NEP cells were treated with 10 ng/ml bromo-deoxyuridine (BrdU, Sigma) in culture medium overnight at 37° C. The following day, media was removed and the cells were exposed to 0.25% trypsin containing 1 mM EDTA (Life Technologies) for 8 minutes at 37° C. Following trypsin treatment, cells were centrifuged for 3 minutes at 1000 rpm. The pellet was then resuspended in L15 media (Life Technologies) containing 0.04% DNase (Worthington Biochemical Corp., Freehold, N.J.). The suspension was triturated with a fire-polished glass pipette and the cells counted with a hemacytometer. The cells were centrifuged one final time to remove DNase and then resuspended in L15 at 20,000 cells/$\mu$l in preparation for transplantation.

Example 6

Immunosuppression and Animal Surgery

Rats were treated with daily injections of cyclosporin (Novartis, East Hanover, N.J.) (10 mg/kg) i.p. beginning the day before surgery and ending at time of sacrifice. All animals sacrificed at 2 and 7 days received transplants of BrdU labeled cells, while those sacrificed at 28 days received unlabeled cells and two injections of BrdU (100 mg/kg, spaced 2 hours apart) one day prior to sacrifice. Non-transplanted animals served as controls with some animals receiving BrdU injections one day prior to sacrifice (N=3). Sterile surgical procedures and animal care were conducted according to IACUC approved guidelines. Adult (250–300 g) male Fisher 344 rats were anesthetized with a mixture of ketamine 65 mg/kg), xylazine (7.5 mg/kg), acepromazine (0.5 mg/kg) and placed in a stereotaxic frame (Stoelting, Wood Dale, Ill.). The nose bar was set 2.7 mm below the intra aural line. A midline incision was made and a 500 $\mu$m hole was created in the skull using a stainless steel dental drill. Following careful exposure of the underlying cortex, a 320 $\mu$m diameter needle was lowered into the brain. All animals received a 3 $\mu$l injection (20,000 cells/$\mu$l) of human NEPs diluted in L15 media injected at 1 $\mu$l/minute in the anterior subventricular zone (SVZa)(N=22) at +1.4 mm bregma, +1.5 mm lateral, −5.0 mm deep from the brain surface, or the caudal striatum (N=14) at −1.4 mm bregma, +4.3 lateral, −5.0 mm deep from brain surface. The needle was left in the brain for 4 minutes to allow for equilibration and then slowly withdrawn. The overlying scalp was then closed with 5/0 silk suture. All animals had access to food and water ad libitum pre- and post-surgery.

Example 7

Histological Procedures

At 2, 7 and 28 days post-transplantation, rats were deeply anesthetized and perfused transcardially with 250 ml of phosphate-buffered saline (PBS, pH 7.4) followed by 250 ml of fresh 4% paraformaldehyde at a rate of 50 ml/minute. The brain was removed and post-fixed overnight in 4% paraformaldehyde at 4° C. The specimens were transferred to neutral-buffered PBS and stored at 4° C. Fifty micron sagittal and horizontal tissue sections were cut in cold 1×PBS using a vibratome (Ted-Pella Inc., Redding, Calif.).

Example 8

Immunostaining

Vibratome sections were permeabilized with 0.5% Triton X-100 (Sigma) in PBS for 30 minutes and immuno-blocked using either a dilute goat (4%) or horse serum (3%) in PBS containing 0.3% triton. Sections stained for BrdU were incubated in ice-cold 0.1N HCl for 10 minutes and then 2.0N HCl for 30 minutes at 37° C. In general, sections were incubated in primary antibody diluted in blocking solution overnight (18–20 hours) at 4° C. The following primary antibodies were used: monoclonal rat anti-BrdU (1:150; Accurate Chemicals, Westbury, N.Y.); monoclonal human-specific anti-mitochondria (anti-hMito; 1:500; Chemicon, Temecula, Calif.); monoclonal human specific against nuclear antigens (anti-hNuc; 1:200; Chemicon); monoclonal against neuronal nuclear antigens (NeuN; 1:220; Chemicon); monoclonal human-specific neural cell adhesion molecule (anti-hNCAM; 1:500; Chemicon); polyclonal antibodies against glial fibrillary acidic protein (GFAP; 1:2000; Dako Corp., Carpinteria, Calif.); monoclonal antibody directed against human GFAP (1:1000; Sternberger Monoclonals, Lutherville, Md.) and monoclonal mouse anti-oligodendrocytes/myelin (MAB 328; 1:1000; Chemicon). Next, the sections were rinsed in PBS and incubated in alexa 488 or alexa 594-conjugated goat anti-mouse IgG1 (1:220 in PBS+0.3% triton) for 1 hour at room temperature to visualize anti-hNuc and anti-NeuN. Alexa-conjugated goat anti-rabbit IgG (Molecular Probes, Eugene, Oreg.) was used to visualize anti-GFAP. Similarly, alexa-conjugated goat anti-mouse IgM was used for MAB 328 staining. Biotinylated secondaries were used to amplify all other reactions at a concentration of 1:220 for 1 hour at room temperature diluted in PBS+0.3% triton. For anti-BrdU, goat anti-rat IgG; anti-hMito, goat anti-mouse IgG1; anti-hNCAM, goat anti-mouse IgG1; anti-hGFAP, goat anti-mouse IgG1 (all biotinylated reagents purchased from Southern Biotech. Assoc., Birmingham, Ala.). Following secondary treatment, a streptavidin-conjugated tertiary was applied to the sections for 50 minutes at room temperature to visualize the reaction. All tertiaries were conjugated to either Texas Red or Alexa 488 (Molecular Probes) and also used as a concentration of 1:220 in PBS. All sections were counterstained with DAPI to identify cell nuclei.

Stained sections were visualized using the appropriate fluorescent filters on a Nikon E600 upright epifluorescent microscope. Representative images were captured using a digital color video camera (CoolSnap, RS Photometrics). For double and triple-stained samples, each image was taken using only one emission filter at t time. Layered montages were then prepared using Adobe Photoshop software on a PC computer.

What is claimed is:

1. A method for isolating human neuroepithelial precursor cells from human fetal neural tissue at a stage at which neurogenesis occurs comprising:

(a) culturing human fetal neural cells at a stage at which neurogenesis occurs in medium containing fibroblast growth factor and chick embryo extract; and (b) immunodepleting from the cultured human fetal neural cells any cells expressing A2B5, NG2 and eNCAM so that an isolated population of human neuroepithelial precursor cells remains.

* * * * *